(12) United States Patent
Hwang et al.

(10) Patent No.: US 9,617,288 B2
(45) Date of Patent: Apr. 11, 2017

(54) METHOD FOR PREPARING RACEMIC OR OPTICALLY ACTIVE α-GLYCEROPHOSPHORYLCHOLINE

(71) Applicant: ENZYTECH, LTD., Daejeon (KR)

(72) Inventors: Soon Ook Hwang, Daejeon (KR); Dae Myoung Yun, Daejeon (KR)

(73) Assignee: ENZYTECH, LTD., Daejeon (KR)

( * ) Notice: Subject to any disclaimer, the term of this patent is extended or adjusted under 35 U.S.C. 154(b) by 0 days.

(21) Appl. No.: 15/116,302

(22) PCT Filed: Feb. 5, 2015

(86) PCT No.: PCT/KR2015/001183
§ 371 (c)(1),
(2) Date: Aug. 3, 2016

(87) PCT Pub. No.: WO2015/119438
PCT Pub. Date: Aug. 13, 2015

(65) Prior Publication Data
US 2017/0008917 A1    Jan. 12, 2017

(30) Foreign Application Priority Data
Feb. 10, 2014   (KR) .......................... 10-2014-0015099

(51) Int. Cl.
*C07F 9/10*    (2006.01)
(52) U.S. Cl.
CPC ............ *C07F 9/10* (2013.01); *C07B 2200/07* (2013.01)
(58) Field of Classification Search
None
See application file for complete search history.

(56) References Cited

U.S. PATENT DOCUMENTS 5,250,719 A    10/1993   Tronconi

FOREIGN PATENT DOCUMENTS

| CN | 101967160 A | * | 2/2011 | ................ C07F 9/09 |
|---|---|---|---|---|
| EP | 0217765 B1 | | 8/1990 | |
| EP | 0468100 B1 | | 3/1995 | |
| KR | 10-0262281 B1 | | 7/2000 | |
| KR | 10-2007-0119176 A | | 12/2007 | |
| KR | 10-2010-0077632 A | | 7/2010 | |
| KR | 10-2011-0066004 A | | 6/2011 | |
| KR | 10-2011-0106720 A | | 9/2011 | |

OTHER PUBLICATIONS

Search Report for International Application No. PCT/KR2015/001183.
Written Opinion for International Application No. PCT/KR2015/001183.
Comfurius P. and Zwaal RF, "The enzymatic synthesis of phosphatidylserine and purification by CM-cellulose column chromatography." Biochim. Biophys. Acta, 488(1):36-42, Jul. 20, 1977.
"Conversion of phosphatidylcholine to phosphatidylserine by various phospholipases D in the presence of L- or D-serine" Biochim. Biophys. Acta, 1003(3):277-283, Jun. 1989.
J. Maurukas et al., "An Improved Synthesis of Glycerylphosphorylcholine" J. Org. Chem., 26:608, 1961.
Erich Baer et al., "L-α-Glycerylphosphorylcholine", Contribution from the Banting and Best Department of Medical Research, University of Toronto, J. Am. Chem. Soc. vol. 70. pp. 1394, Apr. 1948.

* cited by examiner

*Primary Examiner* — Michael Barker
(74) *Attorney, Agent, or Firm* — LRK Patent Law Firm

(57) ABSTRACT

A method of preparing racemic or optically active D or L-α-glycerophosphorylcholine in large amounts by subjecting choline phosphate or a salt thereof, and racemic or optically highly pure (S) or (R)-3-halo-1,2-propanediol to a substitution reaction in a medium at high temperature in the presence of an inorganic base which increases the activity of the reaction. The method is cost-effective because of the use of starting materials which are inexpensive compared to those in a conventional method. Moreover, the method is simple and convenient because it is performed via a one-pot reaction without a separate purification process. In addition, it enables a large amount of racemic or optically active D or L-α-glycerophosphorylcholine, or a salt thereof, to be quantitatively produced in a medium without side reactions by using the inorganic base which increases the reaction activity.

4 Claims, No Drawings

METHOD FOR PREPARING RACEMIC OR OPTICALLY ACTIVE α-GLYCEROPHOSPHORYLCHOLINE

CROSS-REFERENCE TO RELATED APPLICATION(S)

This application claims priority to Korean Patent Application No. 10-2014-0015099, filed Feb. 10, 2014, which is hereby incorporated by reference in its entirety into this application.

BACKGROUND OF THE INVENTION

1. Field of the Invention

The present invention relates to a method for preparing racemic or optically active α-glycerophosphorylcholine, and more particularly to a method of preparing racemic or optically active D or L-α-glycerophosphorylcholine in large amounts by subjecting choline phosphate or a salt thereof and racemic or optically highly pure (S) or (R)-3-halo-1,2-propanediol to a substitution reaction in a medium at high temperature in the presence of an inorganic base which increases the activity of the reaction.

2. Description of Related Art

Racemic or optically active D or L-α-glycerophosphorylcholine, a compound represented by the following Formula 1, is known to have excellent effects on the treatment of secondary symptoms caused by cerebrovascular defects, senile cognitive disorders (memory impairment, distraction, loss of sense of direction, loss of motivation and spontaneity, concentration decline) such as degenerative brain organic psycho-syndrome, and senile pseudo-depression such as emotional and behavioral changes (emotional instability, irritability, lack of attention). In addition, this compound is known as an excellent drug that promotes the production of the brain neurotransmitter acetylcholine to thereby normalize abnormal choline neurotransmission caused by lack of acetylcholine and normalize the function of damaged neurons.

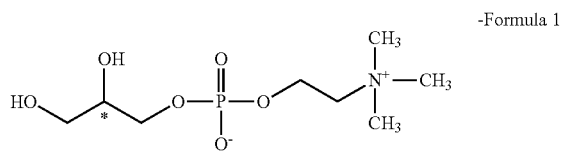 [SMILES: C[N+](C)(C)CCOP(=O)([O-])OCC(O)CO]

-Formula 1 wherein * is a chiral center and refers to a racemic or optically active D or L-α-optical isomer.

The racemic or optically active D or L-α-glycerophosphorylcholine having excellent pharmacological effects as described above can be prepared by organic synthetic methods or can be prepared by deacylating the acyl phospholipids of plants (soy lecithin) or animals (egg yolk or bovine brain), and representative methods for preparation of this compound are as follows.

As shown in Reaction Scheme 1 below, Korean Patent No. 0262281 discloses a method of preparing glycerophosphorylcholine by deacylating a natural or synthetic phospholipid mixture by alcoholysis, followed by treatment with basic ion exchange resin. However, this method is a method of purifying phospholipids from a starting material containing a large amount of impurities by deacylation, and has disadvantages in that it has a low recovery of glycerophosphorylcholine in the preparation of glycerophosphorylcholine and is not suitable for the production of a large amount of glycerophosphorylcholine, due to the use of basic ion exchange resin in the purification process.

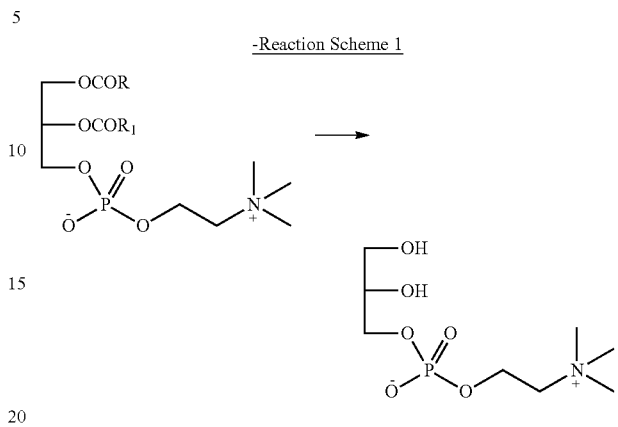

-Reaction Scheme 1 wherein R and $R_1$ may be the same or different and are each independently a $C_{13}$-$C_{25}$ alkyl or a $C_{13}$-$C_{25}$ mono- or polyunsubstituted alkenyl.

U.S. Pat. No. 5,250,719 discloses a process of preparing D or L-α-glycerophosphorylcholine according to a method similar to that shown in Reaction Scheme 1 above. However, this process has disadvantages in that the purification process is complex due to the use of ion exchange resin and in that the recovery of L-α-glycerophosphorylcholine is low.

In European Patent No. 217,765 B1, deoleated soy or egg lecithin is deacylated, and then L-α-glycerophosphorylcholine and L-α-glycerophosphorylcholine ethanolamine are complexed with zinc salt to remove other impurities. The complex is decomposed with pyridine and separated by ion exchange resin, and the mixture of L-α-glycerophosphorylcholine and L-α-glycerophosphorylcholine ethanolamine is also separated by ion exchange resin, thereby preparing L-α-glycerophosphorylcholine. This preparation method has disadvantages in that, because the process of preparing L-α-glycerophosphorylcholine is composed of several steps, the preparation process is complex, and because the purification process comprises the use of ion exchange resin twice, it is inefficient, and also the yield is very low.

In addition, a method of preparing glycerophosphorylcholine by deacylating lecithin extracted from vegetable materials or animal organs is known (Biochim. *Biophys. Acta*, 488:36, 1977; *Biochim. Biophys. Acta*, 1003:277, 1989). However, this method has disadvantages in that, because various by-products such as D-1,2-glycerophosphate are produced depending on deacylation reaction conditions (reaction time, reaction temperature, the kind of base and the kind of solvent), the purification process is complex and the yield is low.

As seen in the above-described known examples, the methods of preparing L-α-glycerophosphorylcholine from materials such as lecithin extracted from plants or animals have an advantage in that materials required for preparation of L-α-glycerophosphorylcholine are readily available in nature. However, because the extracted material contains a large amount of impurities, it is necessary to purify the extracted material using ion exchange resin or the like, and for this reason, the purification process is complex and it is difficult to prepare L-α-glycerophosphorylcholine with high purity. In addition, because the recovery of L-α-glycerophosphorylcholine is low, the methods are uneconomical and are also unsuitable for the production of a large amount of L-α-glycerophosphorylcholine.

Meanwhile, regarding conventional methods of preparing glycerophosphorylcholine by organic synthetic methods, a method of preparing D,L-α-glycerophosphorylcholine using D,L-acetone glycerol as a stating material as shown in Reaction Scheme 2 below is known (*J. Org. Chem.*, 26:608, 1961). However, this method has disadvantages in that, because a total of four reaction steps are carried out, the reaction process is complicated, and because the reactions are carried out under an anhydrous condition, the reaction process is complicated. In particular, there is a disadvantage in that this method is difficult to apply industrially, because the starting material D,L-acetone glycerol is very expansive and because expensive compounds such as palladium and silver carbonate are used to remove a phenyl group and a chlorine ion, which act as protecting groups in the reactions.

-Reaction Scheme 2

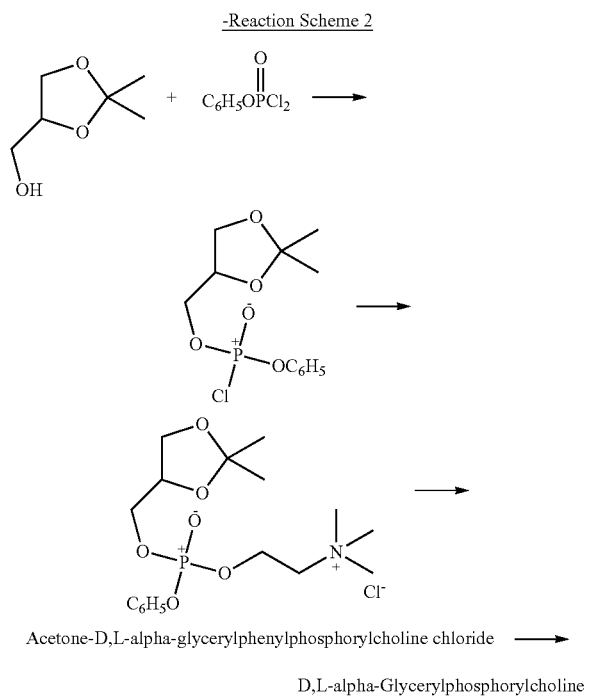

Acetone-D,L-alpha-glycerylphenylphosphorylcholine chloride ⟶

D,L-alpha-Glycerylphosphorylcholine

Furthermore, *J. Am. Chem. Soc.* Vol. 70. pp 1394 (1948) discloses a method of preparing L-α-glycerophosphorylcholine via a method similar to the above-described method.

As shown in Reaction Scheme 3 below, European Patent Publication No. 468100 discloses a method of preparing racemic or L-α-glycerophosphorylcholine from the substitution reaction of isopropylidene glycerol with 2-chloro-2-oxy-3,3,2-dioxaphospholane. However, this method also problems in that expansive isopropylidene glycerol and 2-chloro-2-oxy-3,3,2-dioxaphospholane are used as the starting materials and in that the reaction is carried out under an anhydrous condition, and thus the reaction conditions are strict. In addition, there is a problem in that racemic or L-α-glycerophosphorylcholine must be finally purified by ion exchange resin after hydrolysis.

-Reaction Scheme 3

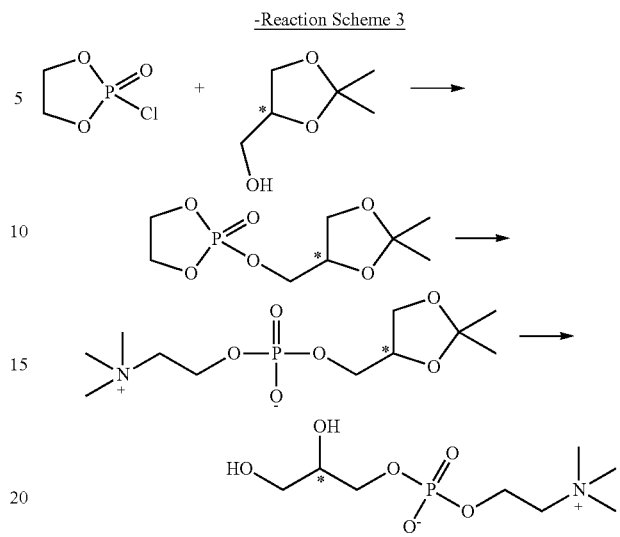

wherein * is a chiral center and refers to a racemic or L-form optical isomer.

Korean Patent Application Publication No. 2011-0066004 discloses a method comprising a step of reacting a phosphorylcholine chloride calcium salt with an alkali metal base in an aqueous solution to produce an alkali metal-substituted salt, followed by a reaction with glycidol without separating the alkali metal-substituted salt.

-Reaction Scheme 4

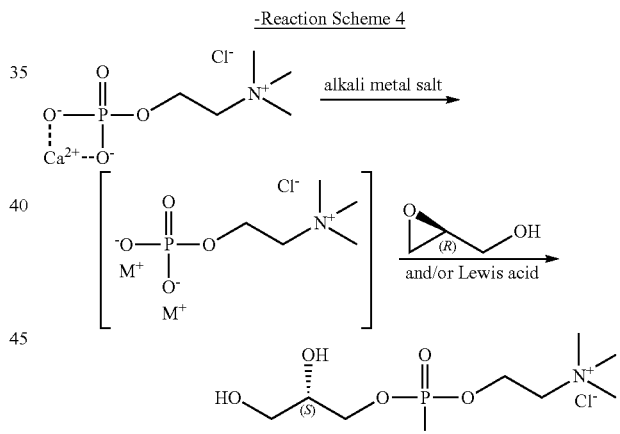

wherein $M^+$ represents an alkali metal such as lithium, sodium or potassium, and $Cl^-$ represents chlorine.

The preparation process shown in Reaction Scheme 4 above is a process of preparing L-α-glycerophosphorylcholine through a ring-opening reaction by reacting a phosphorylcholine chloride calcium salt with (R)-glycidol under reflux in an aqueous solution at high temperature. However, (R)-glycidol is unstable and likely to be decomposed at high temperature, resulting in an increase in the production of by-products, and for this reason, the reaction yield is low, and it is difficult to purify L-α-glycerophosphorylcholine with high purity. In addition, because of various problems, including a process of removing insoluble salts in a final step and the addition of purification by ion exchange resin for removing ions, many problems arise in preparing L-α-glycerophosphorylcholine in large amounts by the preparation process of Reaction Scheme 4.

In a method disclosed in Korean Patent Application Publication No. 2007-0119176, as shown in Reaction Scheme 5 below, phosphorylcholine chloride calcium tetrahydrate is treated with oxalic acid, sulfuric acid or EDTA in an aqueous solution to remove the calcium salt, and then as shown in Reaction Scheme 6 below, the resulting phosphorylcholine chloride is reacted with (R)-glycidol in an organic solvent, and impurities are removed therefrom by use of an organic solvent and ion exchange resin, thereby obtaining L-α-glycerophosphorylcholine.

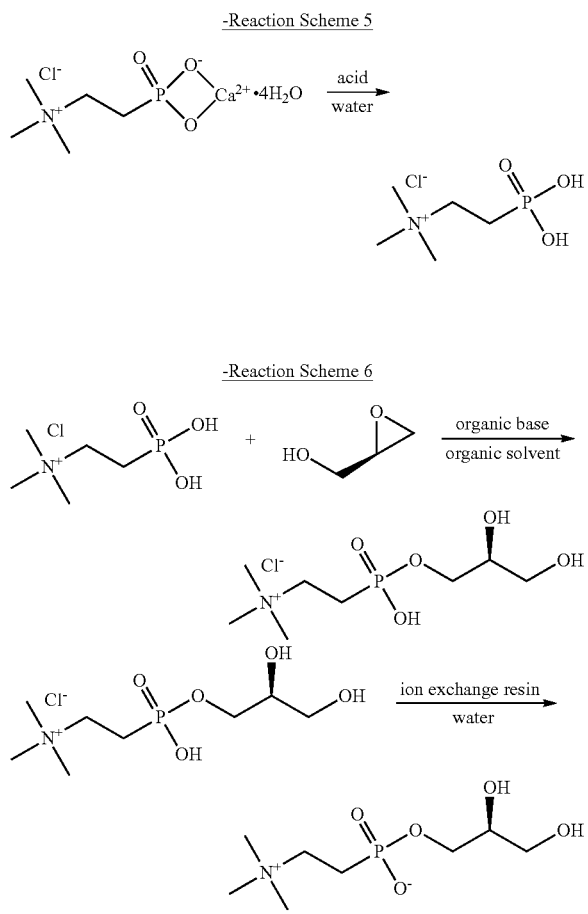

In the preparation process shown in Reaction Schemes 5 and 6 above, there is a problem in that the calcium salt can remain depending on the pH or temperature of the reactant used in removal of the calcium salt from phosphorylcholine chloride calcium tetrahydrate so that it can interfere with a subsequent reaction to thereby reduce the yield. In addition, because the reaction with (R)-glycidol is carried out, (R)-glycidol is unstable and likely to be decomposed, resulting in an increase in the production of by-products, it is difficult to purify L-α-glycerophosphorylcholine with high purity. Furthermore, there is a problem in that the step of using the organic solvent and the ion exchange resin after completion of the reaction is complex.

In a method disclosed in Korean Patent Application Publication No. 2011-0106720, as shown in Reaction Scheme 7 below, optically active (R)-3-chloro-1,2-propanediol is reacted with a solution of a potassium hydroxide, sodium hydroxide or potassium carbonate base in distilled water in the presence of a methanol or ethanol solvent at a temperature of −10° C. to 0° C. to synthesize the intermediate (R)-glycidol, and the synthesized glycidol is subjected to a ring-opening reaction with choline phosphate or its salt at a temperature of 50° C. to 60° C., thereby preparing L-α-glycerophosphorylcholine.

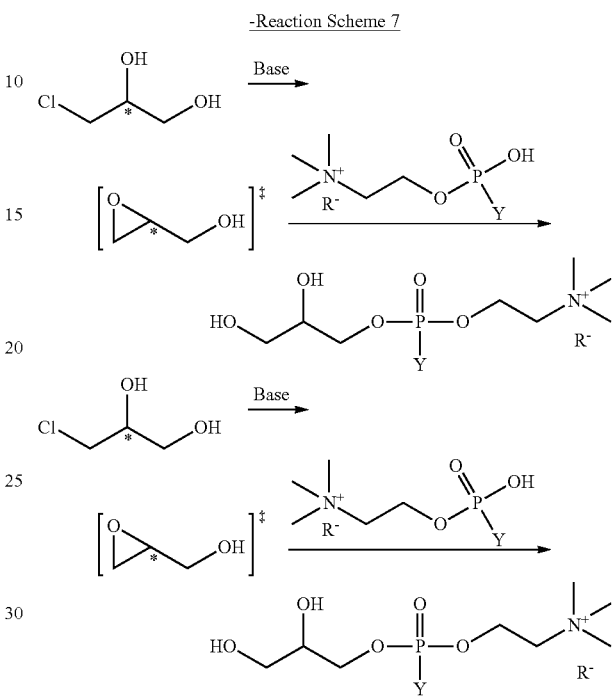

wherein * is a chiral center, Y is OH or O⁻; and R⁻ is a halogen atom, an anion (X⁻) or null.

However, in the preparation process shown in Reaction Scheme 7 above, problems may arise in that unreacted (R)-3-chloro-1,2-propanediol remains after the reaction of (R)-3-chloro-1,2-propanediol with (R)-glycidol and in that when (R)-glycidol is reacted, the production of glycerin increases with the passage of the reaction time, making it difficult to remove the glycerin. In addition, there are problems in that, because the intermediate (R)-glycidol is unstable and likely to be decomposed, resulting in an increase in the production of by-products, the reaction yield is low, and it is difficult to purify L-α-glycerophosphorylcholine. Thus, there are many problems in preparing L-α-glycerophosphorylcholine in large amounts.

Accordingly, the present inventors have made extensive efforts to overcome the above-described problems occurring in the prior art, and, as a result, have found that when choline phosphate or a salt thereof and racemic or optically highly pure (S) or (R)-3-halo-1,2-propanediol are subjected to a substitution reaction in a medium at high temperature in the presence of an inorganic base which increases the activity of the reaction, D or L-α-glycerophosphorylcholine can be prepared without a process of producing the intermediate (R)-glycidol, and also have found that D or L-α-glycerophosphorylcholine can be economically and easily prepared with high purity in high yield without having to perform a separate purification process, thereby completing the present invention.

SUMMARY OF THE INVENTION

An object of the present invention is to provide a method capable of preparing a large amount of racemic or optically active D or L-α-glycerophosphorylcholine having high optical purity via a simple process in a cost-effective manner.

In order to accomplish the above object, the present invention provides a method for preparing a racemic or optically active D or L-α-glycerophosphorylcholine represented by the following Formula 1, the method comprising subjecting a choline phosphate represented by the following Formula 2 or a salt thereof and an (S) or (R)-3-halo-1,2-propanediol represented by the following Formula 3 to a substitution reaction in a medium at a temperature of 60° C. to 100° C., thereby preparing the racemic or optically active D or L-α-glycerophosphorylcholine via a one-pot reaction without an (R)-glycidol intermediate production process:

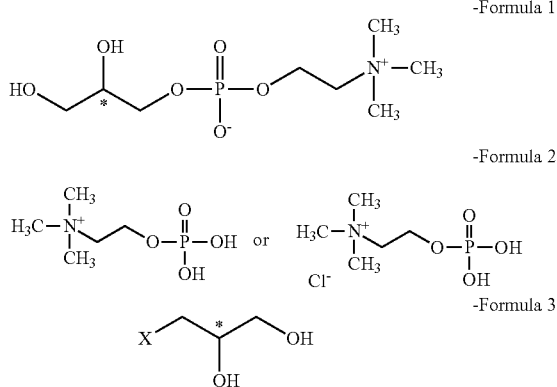

wherein * is a chiral center, Formula 1 represents a racemic or optically active D or L-α-glycerophosphorylcholine isomer, Formula 2 represents choline phosphate or a salt thereof; and X in Formula 3 denotes fluorine, chlorine, bromine or iodine.

DETAILED DESCRIPTION OF THE INVENTION

Unless defined otherwise, all technical and scientific terms used herein have the same meaning as commonly understood by one of ordinary skill in the art to which the present invention pertains. Generally, the terms used therein are those that are well known in the art and generally used.

One aspect of the present invention is directed to a method for preparing a racemic or optically active D or L-α-glycerophosphorylcholine represented by the following Formula 1, the method comprising subjecting a choline phosphate represented by the following Formula 2 or a salt thereof and an (S) or (R)-3-halo-1,2-propanediol represented by the following Formula 3 to a substitution reaction in a medium at a temperature of 60° C. to 100° C., thereby preparing the racemic or optically active D or L-α-glycerophosphorylcholine via a one-pot reaction without an (R)-glycidol intermediate production process:

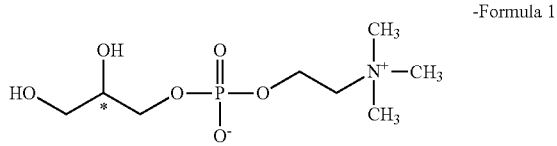

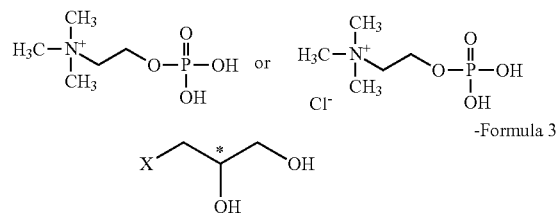

wherein * is a chiral center, Formula 1 represents a racemic or optically active D or L-α-glycerophosphorylcholine isomer, Formula 2 represents choline phosphate or a salt thereof, and X in Formula 3 denotes fluorine, chlorine, bromine or iodine.

As used herein, the term "one-pot reaction" means synthesizing a desired product via a one-step process without performing a plurality of steps. In the preparation method of the present invention, although racemic or optically highly pure (S) or (R)-3-halo-1,2-propanediol is used as a starting material, a large amount of racemic or optically active D or L-α-glycerophosphorylcholine or a salt thereof can be produced with high purity in high yield via a direct substitution reaction without synthesizing the intermediate (R)-glycidol, unlike the method disclosed in Korean Patent Application Publication No. 2011-01067.

A process for preparing the racemic or optically active D or L-α-glycerophosphorylcholine represented by Formula 1 or a salt thereof according to the present invention can be summarized briefly as shown in Reaction Scheme 8 below:

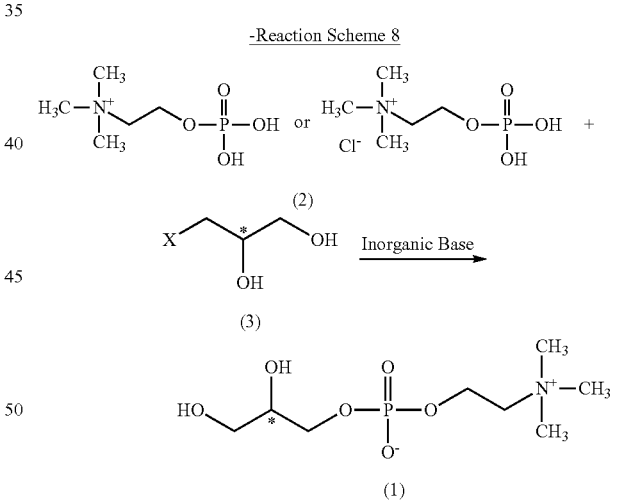

wherein * denotes a chiral center, (1) represents a racemic or optically active D or L-α-glycerophosphorylcholine isomer; (2) represents choline phosphate or a salt thereof; and X in (3) denotes fluorine, chlorine, bromine or iodine.

As shown in Reaction Scheme 8 above, in the process of preparing the racemic or optically active D or L-α-glycerophosphorylcholine represented by Formula 1 or a salt thereof, the racemic or optically highly pure (S) or (R)-3-halo-1,2-propanediol represented by Formula 3 is subjected to a substitution reaction with choline phosphate or a salt thereof in a medium. In the substitution reaction, an organic base is used to increase the activity of the reaction.

In the present invention, the racemic or optically active (S) or (R)-3-halo-1,2-propanediol represented by Formula 3 may be added in an amount of 1-5 equivalents based on the choline phosphate represented by Formula 2 or a salt thereof. Preferably, it is used in an amount of 1-2 equivalents. If the racemic or optically active (S) or (R)-3-halo-1,2-propanediol is added in an amount of less than 1 equivalent based on the choline phosphate or a salt thereof, there will be a problem in that the reaction does not proceed, and if the racemic or optically active (S) or (R)-3-halo-1,2-propanediol is added in an amount of more than 5 equivalents, there will be a problem in that an excessive amount of unreacted racemic or optically active (S) or (R)-3-halo-1,2-propanediol remains, resulting in cost-ineffectiveness, and must be removed.

In the present invention, the racemic or optically active (S) or (R)-3-halo-1,2-propanediol represented by Formula 3 may be selected from among various compounds depending on the kind of X (fluorine, chlorine, bromine or iodine). In the present invention, (S) or (R)-3-chloro-1,2-propanediol is preferably used.

In the present invention, the inorganic base which is added in order to increase the activity of the reaction may be one or more selected from the group consisting of sodium hydroxide, potassium hydroxide, calcium hydroxide, magnesium hydroxide, barium hydroxide, lithium hydroxide, sodium carbonate, sodium bicarbonate, potassium carbonate, potassium bicarbonate, and mixtures thereof. Preferably, it may be potassium hydroxide or potassium carbonate, and these inorganic bases may be used alone or in combination.

The inorganic base may be used in an amount of 1-5 equivalents, preferably 1-3 equivalents, based on the reactants. If the inorganic base is added in an amount of less than 1 equivalent based on the reactants, problems will arise in that the reaction rate is slow and unreacted material occurs, and if the inorganic base is added in an amount of more than 5 equivalents, there will be problems in that by-products increase, and thus a separate purification process is required and the reaction yield decreases.

In the present invention, the substitution reaction may be performed at a temperature of 60° C. to 100° C., preferably 60° C. to 80° C., for 2-48 hours, preferably 5-24 hours. If the reaction temperature is lower than 60° C. or higher than 100° C., by-products will increase, and thus the reaction yield will be reduced and a separate purification process will be required.

In the present invention, the medium may be selected from the group consisting of methanol, ethanol, propanol, isopropanol, butanol, isobutanol, tert-butanol, acetone, tetrahydrofuran, dioxane, dimethylformamide, dimethylacetamide, dimethyl sulfoxide, acetonitrile, diethylether, ethyl acetate, dimethylacetamide, and mixtures thereof. In the present invention, methanol or ethanol is preferably used as the medium.

In an example of the present invention, racemic or optically active D or L-α-glycerophosphorylcholine was prepared using the method shown in Reaction Scheme 8 according to the present invention, and experiments were performed under various conditions in order to prepare optically active L-α-glycerophosphorylcholine by performing a one-spot reaction consisting of a substitution reaction in a medium in the presence of an inorganic base which increases the activity of the reaction.

Optically active L-α-glycerophosphorylcholine and racemic α-glycerophosphorylcholine were prepared, and, as a result, it was found that the two compounds could all be obtained in a yield of 97% or higher. In addition, in a comparative example, racemic α-glycerophosphorylcholine was prepared using the method that comprises producing the intermediate (R)-glycidol as disclosed in Korean Patent Application Publication No. 2011-01067. As a result, a yield of up to 58% was shown, indicating that the efficiency with which racemic α-glycerophosphorylcholine is prepared according to the comparative example is significantly lower than that in the preparation method of the present invention (Table 1).

Furthermore, in order to confirm whether the intermediate (R)-glycidol is not actually produced when racemic or optically active D or L-α-glycerophosphorylcholine is prepared by the preparation method of the present invention, an experiment was performed. As a result, it could be seen that, in the case of Comparative Example 2, 3-chloro-1,2-propanediol was converted to the immediate (R)-glycidol (Table 3), and the production of the by-product glycerin increased as the reaction time increased, whereas in the case of the preparation method of the present invention, the intermediate (R)-glycidol was not substantially produced, and the amount of the by-product glycerin did not increased even when the reaction time increased (Table 2). This suggests that the preparation method of the present invention enables racemic or optically active D or L-α-glycerophosphorylcholine to be prepared directly via a one-pot reaction without producing the intermediate (R)-glycidol.

Hereinafter, the present invention will be described in further detail with reference to examples. It will be obvious to those skilled in the art that these examples are for illustrative purposes only and are not intended to limit the scope of the present invention.

EXAMPLES

Example 1

Preparation of Racemic or Optically Active α-Glycerophosphorylcholine in the Presence of Inorganic Base In order to prepare optically active L-α-glycerophosphorylcholine by performing a one-pot reaction based on a substitution reaction in a medium in the presence of an inorganic base which increases the activity of the reaction, experiments were performed under various conditions.

1-1

Preparation of Optically Active L-α-Glycerophosphorylcholine

In a 500-ml three-neck round bottom flask equipped with a thermometer, a reflux condenser and a stirrer, 10 g of phosphorylcholine chloride (1 equivalent 228 mmol) was dissolved in 200 ml of methanol. Then, 5.1 g of potassium hydroxide (2 equivalents, 455 mmol) was added slowly to the reaction solution, followed by stirring for 1 hour. Then, the reaction solution was heated to 60° C., after which 10 g of (R)-3-chloro-1,2-propanediol (2 equivalents, 452 mmol) was added slowly thereto, followed by reflux for 24 hours, thereby performing a substitution reaction.

After completion of the reaction, the reaction solution was concentrated under reduced pressure, and the concentrate was diluted with 10 ml of water, and then washed twice with ethyl acetate. Then, the aqueous layer was concentrated tinder reduced pressure, thereby obtaining 11.4 g (97% yield) of L-α-glycerophosphorylcholine.

The results of NMR analysis of the prepared L-α-glycerophosphorylcholine are as follows:

$^1$H NMR (D$_2$O, 300 MHz): δ 3.23 (s, 9H), 3.65 (m, 4H), 3.91 (m, 4H), 4.29 (m, 2H).

1-2

Preparation of Optically Active L-α-Glycerophosphorylcholine

In a 500-ml three-neck round bottom flask equipped with a thermometer, a reflux condenser and a stirrer, 10 g of phosphorylcholine chloride (1 equivalent, 228 mmol) was dissolved in 200 ml of methanol. Then, 5.1 g of potassium hydroxide (2 equivalents, 455 mmol) was added slowly to the reaction solution, followed by stirring for 1 hour. Then, the reaction solution was heated to 65° C., after which 10 g of (R)-3-chloro-1,2-propanediol (2 equivalents, 452 mmol) was added slowly thereto, followed by reflux for 16 hours, thereby performing a substitution reaction.

After completion of the reaction, the reaction solution was concentrated under reduced pressure, and the concentrate was diluted with 10 ml of water, and then washed twice with acetone. Then, the aqueous layer was concentrated under reduced pressure, thereby obtaining 11.60 g (99% yield) of L-α-glycerophosphorylcholine.

The results of NMR analysis of the prepared L-α-glycerophosphorylcholine are the same as the analysis results described in Example 1.

1-3

Preparation of Racemic α-Glycerophosphorylcholine

In a 1000-ml three-neck round bottom flask equipped with a thermometer and a stirrer, 50 g of phosphorylcholine chloride (1 equivalent, 456 mmol) was dissolved in 500 ml of methanol. Then, 25.5 g of potassium hydroxide (2 equivalents, 910 mmol) was added slowly to the reaction solution, followed by stirring for 1 hour. Then, the reaction solution was heated slowly to 65° C., after which 50 g of racemic 3-chloro-1,2-propanediol (2 equivalents, 910 mmol) was added slowly thereto, followed by reflux for 16 hours, thereby performing a substitution reaction.

After completion of the reaction, the reaction solution was concentrated under reduced pressure, and the concentrate was diluted with 50 ml of water, and then washed twice with acetone. Then, the aqueous layer was concentrated under reduced pressure, thereby obtaining 57.02 g (97% yield) of racemic α-glycerophosphorylcholine.

The results of NMR analysis of the prepared racemic α-glycerophosphorylcholine are the same as the analysis results described in Example 1.

1-4

Preparation of Racemic α-Glycerophosphorylcholine

In a 250-ml three-neck round bottom flask equipped with a thermometer, a reflux condenser and a stirrer, 10 g of phosphorylcholine chloride (1 equivalent, 569 mmol) was dissolved in 20 ml of ethanol. Then, 3.07 g of potassium hydroxide (1.2 equivalents, 683 mmol) was added slowly to the reaction solution, followed by addition of 40 ml of acetonitrile. The reaction solution was heated slowly to 80° C. and stirred at that temperature for 30 minutes, after which 7.55 g of racemic 3-chloro-1,2-propanediol (1.5 equivalents, 854 mmol) was added slowly to the stirred reaction solution, followed by reflux for 19 hours, thereby performing a substitution reaction.

After completion of the reaction, the reaction solution was concentrated under reduced pressure, and the concentrate was diluted with 100 ml of water, and then washed twice with ethyl acetate. Then, the aqueous layer was concentrated under reduced pressure, thereby obtaining 11.52 g (98% yield) of racemic α-glycerophosphorylcholine.

The results of NMR analysis of the prepared racemic α-glycerophosphorylcholine are the same as the analysis results described in Example 1.

1-5

Comparative Example 1

Preparation of Racemic α-Glycerophosphorylcholine After Preparation of Glycidol from Racemic 3-Chloro-1,2-Propanediol in the Presence of Inorganic Base (Korean Patent Application Publication No. 2011-0106720)

In a 500-ml three-neck round bottom flask equipped with a thermometer, a reflux condenser and a stirrer, 25 g of racemic 3-chloro-1,2-propanediol (1 equivalent, 900 mmol) was dissolved in 200 ml of ethanol, and then cooled to a temperature between −15° C. and −10° C. A solution of 9.05 g of sodium hydroxide (1 equivalent, 900 mmol) in 10 ml of distilled water was added slowly to the cooled solution such that the internal temperature would be maintained at a temperature between −5° C. and 0° C., followed by stirring at the same temperature for about 1 hour.

Next, 24.83 g of phosphorylcholine chloride (0.5 equivalents, 450 mmol) was added to the reaction solution, followed by stirring at 53° C. for 27 hours, thereby preparing racemic α-glycerophosphorylcholine.

TABLE 1

Production of α-glycerophosphorylcholine as a function of reaction time

|  | PC-Cl | GPC |
| --- | --- | --- |
| 0 hr | 100% | 0% |
| 2 hr | 88.0% | 12.0% |
| 5 hr | 77.2% | 22.8% |
| 20 hr | 57.4% | 42.6% |
| 27 hr | 42.0% | 58.0% |

The remaining amount of phosphorylcholine chloride (PC—Cl) and the amount of racemic α-glycerophosphorylcholine produced were measured as a function of reaction time, and, as a result, α-glycerophosphorylcholine was produced in a yield of up to 58% (Table 1).

Example 2

Production of Glycidol and Glycerin from Racemic 3-Chloro-1,2-Propanediol in the Presence of Inorganic Base In order to confirm whether the intermediate (R)-glycidol is not actually produced when racemic or optically active D or L-α-glycerophosphorylcholine is prepared by the preparation method of the present invention, experiments were performed.

The production of glycidol and glycerin from racemic 3-chloro-1,2-propanediol in the presence of an inorganic base was analyzed. In a comparative example performed using the method disclosed in Korean Patent Application Publication No. 2011-0106720, the production of (R)-glycidol and glycerin from racemic 3-chloro-1,2-propanediol was analyzed.

2-1

Production of Glycidol and Glycerin from Racemic 3-Chloro-1,2-Propanediol in the Presence of Inorganic Base In a 250-ml three-neck round bottom flask equipped with a thermometer and a stirrer, 2.53 g of potassium hydroxide (1 equivalent, 452 mmol) was dissolved in 100 ml of methanol, and then heated to 65° C. and stirred at that temperature. Next, 5 g of racemic 3-chloro-1,2-propanediol (1 equivalent, 452 mmol) was added slowly to the reaction solution, followed by stirring for 23 hours. During stirring, the amounts of glycerin, (R)-glycidol and 3-chloro-1,2-propanediol were measured at various time points (Table 2).

TABLE 2

Amounts of glycerin, (R)-glycidol and 3-chloro-1,2-propanediol

|  | Glycerin | Glycidol | CPD |
|---|---|---|---|
| 1 hr | 3.0% | 27.0% | 70.0% |
| 4 hr | 3.2% | 15.1% | 81.7% |
| 8 hr | 4.1% | 17.7% | 78.2% |
| 23 hr | 2.9% | 18.5% | 78.6% |

As a result, it could be seen that the intermediate (R)-glycidol was not substantially produced and that the amount of the by-product glycerin did not increase even when the reaction time increased. This suggests that the preparation method of the present invention enables racemic or optically active D or L-α-glycerophosphorylcholine to be prepared directly via a one-pot reaction without producing the intermediate (R)-glycidol, unlike other conventional technology (Korean Patent Application Publication No. 2011-0106720).

2-2

Comparative Example 2

Production of Glycidol and Glycerin from Racemic 3-Chloro-1,2-Propanediol in the Presence of Inorganic Base (see Korean Patent Application Publication No. 2011-0106720)

In a 500-ml three-neck round bottom flask equipped with a thermometer and a stirrer, 25 g of racemic 3-chloro-1,2-propanediol (1 equivalent, 900 mmol) was dissolved in 200 ml of ethanol, and then cooled to a temperature between −15° C. and −10° C. A solution of 9.05 g of sodium hydroxide (1 equivalent, 900 mmol) in 10 ml of distilled water was added slowly to the cooled solution such that the internal temperature would be maintained at a temperature between −5° C. and 0° C., followed by stirring at the same temperature for 21 hours, thereby preparing an (R)-glycidol intermediate.

After completion of the reaction, the amount of glycerin produced, the amount of 3-chloro-1,2-propanediol remaining after the reaction, and the amount of (R)-glycidol produced were measured, and the results of the measurement are shown in Table 3 below.

TABLE 3

Amounts of glycerin, (R)-glycidol and 3-chloro-1,2-propanediol

|  | Glycerin | Glycidol | CPD |
|---|---|---|---|
| 0 hr | 0% | 0% | 100% |
| 1 hr | 6.6% | 91.8% | 1.6% |
| 3 hr | 10.0% | 88.2% | 1.8% |
| 6 hr | 18.3% | 79.3% | 2.4% |
| 21 hr | 52.7% | 43.1% | 4.3% |

As a result, it could be seen that 3-chloro-1,2-propanediol was converted to the intermediate (R)-glycidol and that the production of the by-product glycerin increased as the reaction time increased.

INDUSTRIAL APPLICABILITY

The method for preparing racemic or optically active D or L-α-glycerophosphorylcholine according to the present invention is cost-effective because of the use of starting materials which are inexpensive compared to those in a conventional method. Moreover, the method of the present invention is simple and convenient because it is performed via a one-pot reaction without a separate purification process. In addition, it enables a large amount of racemic or optically active D or L-α-glycerophosphorylcholine or a salt thereof to be quantitatively produced in a medium without side reactions by using an inorganic base which increases the activity of the reaction.

Although the present disclosure has been described in detail with reference to the specific features, it will be apparent to those skilled in the art that this description is only of a preferred embodiment thereof, and does not limit the scope of the present invention. Thus, the substantial scope of the present invention will be defined by the appended claims and equivalents thereof.

The invention claimed is:

1. A method for preparing a racemic or optically active D or L-α-glycerophosphorylcholine represented by the following Formula 1, the method comprising subjecting a choline phosphate represented by the following Formula 2 or a salt thereof, and an (S) or (R)-3-halo-1,2-propanedion represented by the following Formula 3 to a substitution reaction in a medium at a temperature of 60° C. to 100° C., thereby preparing the racemic or optically active D or L-α-glycerophosphorylcholine via a one-pot reaction without an (R)-glycidol intermediate production process:

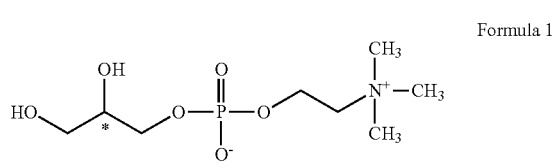

Formula 1

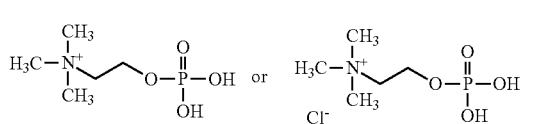

Formula 2

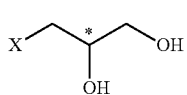

Formula 3 wherein * is a chiral center; Formula 1 represents a racemic or optically active D or L-α-glycerophosphorylcholine isomer; Formula 2 represents choline phosphate or a salt thereof; and X in Formula 3 denotes fluorine, chlorine, bromine or iodine.

2. The method of 1, wherein an inorganic base is additionally used in the substitution reaction to increase activity of the reaction.

3. The method of claim 2, wherein the inorganic base is selected from the group consisting of sodium hydroxide, potassium hydroxide, calcium hydroxide, magnesium hydroxide, barium hydroxide, sodium carbonate, sodium bicarbonate, potassium carbonate, potassium bicarbonate, and mixtures thereof.

4. The method of claim 1, wherein the medium is selected from the group consisting of methanol, ethanol, propanol, isopropanol, butanol, isobutanol, tert-butanol, acetone, tetrahydrofuran, dioxane, dimethylformamide, dimethylacetamide, dimethyl sulfoxide, acetonitrile, diethylether, ethyl acetate, dimethylacetamide, and mixtures thereof.

* * * * *